(12) United States Patent
Syeda-Mahmood (10) Patent No.: US 9,165,115 B2
(45) Date of Patent: Oct. 20, 2015

(54) FINDING TIME-DEPENDENT ASSOCIATIONS BETWEEN COMPARATIVE EFFECTIVENESS VARIABLES

(71) Applicant: International Business Machines Corporation, Armonk, NY (US)

(72) Inventor: Tanveer Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 302 days.

(21) Appl. No.: 13/755,868

(22) Filed: Jan. 31, 2013

(65) Prior Publication Data

US 2014/0214870 A1 Jul. 31, 2014

(51) Int. Cl.
G06F 17/30 (2006.01)
G06F 19/00 (2011.01)

(52) U.S. Cl.
CPC ...... *G06F 19/3443* (2013.01); *G06F 17/30386* (2013.01); *G06F 19/345* (2013.01)

(58) Field of Classification Search
CPC .......... G06F 17/30386; G06F 19/3443; G06F 19/345
USPC ............................ 707/705, 736, 758; 705/2, 3
See application file for complete search history.

(56) References Cited

U.S. PATENT DOCUMENTS

| | | | |
|---|---|---|---|
| 7,127,407 B1 | 10/2006 | Averill et al. | |
| 8,200,682 B2 * | 6/2012 | Suntinger et al. | 707/758 |
| 2002/0065459 A1 * | 5/2002 | MacAdam et al. | 600/424 |
| 2003/0162301 A1 * | 8/2003 | Noergaard et al. | 436/172 |
| 2004/0260155 A1 | 12/2004 | Ciarniello et al. | |
| 2009/0106004 A1 | 4/2009 | Edwards et al. | |
| 2009/0258848 A1 * | 10/2009 | Chakravarti et al. | 514/177 |
| 2012/0303284 A1 * | 11/2012 | Leontovich et al. | 702/19 |
| 2013/0122504 A1 * | 5/2013 | Andersen et al. | 435/6.12 |
| 2014/0074506 A1 * | 3/2014 | Oliver et al. | 705/3 |

FOREIGN PATENT DOCUMENTS

WO 9117510 11/1991

OTHER PUBLICATIONS

Imamura et al., "Reliability of a Comorbidity measure: The index of co-existent disease (ICED)", Journal of Clinical Epidemiology, Sep. 1997, pp. 1011-11016, vol. 50, Issue 9, London, England.

Groot et al., "How to measure Comorbidity: A critical review of available methods", Journal of Clinical Epidemiology 56, 2003, pp. 221-229, Amsterdam, The Netherlands.

Mnatzaganian et al., "Accuracy of Hospital Morbidity data and the Performance of Comorbidity Scores as Predictors of Mortality", Journal of Clinical Epidemiology, pp. 107-115, vol. 65, No. 1, Digital Object Identifier: 10.1016/j.jclinepi.2011.03.014.

(Continued)

*Primary Examiner* — Hares Jami
(74) *Attorney, Agent, or Firm* — Ference & Associates LLC (57) ABSTRACT

Embodiments of the invention relate to arrangements for ascertaining time-dependent associations between inputted comparative effectiveness research (CER) variables from patient data are. Each CER variable is represented via at least one unit time series, and a similarity metric with respect to pairs of CER variables is determined. The determining includes comparing at least one unit time series from each of at least two CER variables.

20 Claims, 5 Drawing Sheets

(56) References Cited

OTHER PUBLICATIONS

Holman et al., "A Multipurpose Comorbidity Scoring System Performed Better than the Charlson Index", Journal of Clinical Epidemiology, Oct. 2005, pp. 1006-1014, vol. 58, Issue 10, Crawley, Australia.

Ward et al., "Pooled Time-Series Regression-Analysis in Longitudinal-Studies", Journal of Clinical Epidemiology, 1993, pp. 645-659, vol. 46, No. 7, California, USA.

Charlson et al., "A New Method of Classifying Prognostic Comorbidity in Longitudinal Studies: Development and Validation", J Chronic Dis, pp. 373-383, 1987, vol. 40, No. 5, Great Britain.

* cited by examiner

| | | Ranked correlations: Mitral stenosis case (394.0) |
|---|---|---|
| - | 0.710 | 401.99 | Unspecified hypertension |
| - | 0.684 | 272.4 | Other and unspecified hyperlipidemia |
| - | 0.605 | 424.0 | Mitral valve disorders |
| - | 0.578 | 427.31 | Atrial fibrillation |
| - | 0.447 | 428.0 | Congestive heart failure, unspecified |
| - | 0.394 | 250.00 | Diabetes mellitus without mention of complication |
| - | 0.315 | 414.01 | Coronary atherosclerosis of native coronary artery |
| - | 0.289 | 443.9 | Peripheral vascular disease, unspecified |
| - | 0.263 | 424.1 | Aortic valve disorders |
| - | 0.210 | 428.1 | Left heart failure |
| - | 0.210 | 244.9 | Unspecified hypothyroidism |
| - | 0.210 | V58.61 | Long-term (current) use of anticoagulants |
| - | 0.184 | 412 | Old myocardial infarction |
| - | 0.184 | V43.3 | Heart valve replaced by other means |
| - | 0.157 | 782.3 | Edema |
| - | 0.157 | 250.60 | Diabetes with neurological manifestations |
| - | 0.157 | 250.40 | Diabetes mellitus with renal manifestations |
| - | 0.131 | 414.00 | Coronary atherosclerosis of unspecified type of vessel |
| - | 0.131 | 424.2 | Tricuspid valve disorders, specified as nonrheumatic |
| - | 0.131 | 436 | Acute, but ill-defined, cerebrovascular disease |

FINDING TIME-DEPENDENT ASSOCIATIONS BETWEEN COMPARATIVE EFFECTIVENESS VARIABLES

BACKGROUND

Generally, large-scale electronic medical record systems are known to offer a wealth of data for comparative effectiveness research and clinical decision support. Rich data in such systems include information about diagnosis, demographics, vitals, diagnostic exams and tests, treatment history and outcomes of patients which can be used to explore many scientific questions.

One such question involves finding statistically meaningful co-morbidity relations between diseases using statistics from the population. Traditionally, co-morbidities have been studied through targeted research on candidate disease pairs, such as heart disease with diabetes within population of patients diagnosed with those diseases where the nature of the relationship is at least known. Next, obtaining meaningful results from large-scale disease-association studies usually depends on the accuracy and completeness of information recorded in an electronic medical record (EMR). Diagnosis codes often subsume many conditions (e.g., congestive heart failure), or are generic in nature (e.g., relate generally to mitral valve disorders), so that they alone are not very reliable indicators of the actual underlying disease. Additional diagnosis inferences must be made from the clinical information recorded in EMR such as in textual reports or using multiple sources of evidence for a disease such as through medications prescribed. Extracting such information from free text in textual reports using natural language processing techniques has only met with limited success. Finally, the choice of the data mining algorithm can also affect the co-morbidities that can be discovered.

Popular association mining methods, such as a priori methods, can generate many spurious associations as they exhaustively search through combinations. Methods that count primarily the frequency of co-occurrences of diseases can sometimes lead to incorrect causative inferences, such as those for diseases that persist in time and are common across many patients, e.g., hypertension. Attempts to handle a time-varying nature of relationships in data mining methods has also been limited in using discrete interval combinations.

BRIEF SUMMARY

Embodiments of the invention relate to arrangements for ascertaining time-dependent associations between inputted comparative effectiveness research (CER) variables from patient data are. In one aspect of the invention, each CER variable is represented via at least one unit time series, and a similarity metric with respect to pairs of CER variables is determined. The determining includes comparing at least one unit time series from each of at least two CER variables.

For a better understanding of exemplary embodiments of the invention, together with other and further features and advantages thereof, reference is made to the following description, taken in conjunction with the accompanying drawings, and the scope of the claimed embodiments of the invention will be pointed out in the appended claims.

DETAILED DESCRIPTION

It will be readily understood that the components of the embodiments of the invention, as generally described and illustrated in the figures herein, may be arranged and designed in a wide variety of different configurations in addition to the described exemplary embodiments. Thus, the following more detailed description of the embodiments of the invention, as represented in the figures, is not intended to limit the scope of the embodiments of the invention, as claimed, but is merely representative of exemplary embodiments of the invention.

Reference throughout this specification to "one embodiment" or "an embodiment" (or the like) means that a particular feature, structure, or characteristic described in connection with the embodiment is included in at least one embodiment of the invention. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in at least one embodiment. In the following description, numerous specific details are provided to give a thorough understanding of embodiments of the invention. One skilled in the relevant art may well recognize, however, that the various embodiments of the invention can be practiced without at least one of the specific details thereof, or can be practiced with other methods, components, materials, et cetera. In other instances, well-known structures, materials, or operations are not shown or described in detail to avoid obscuring aspects of the invention.

The description now turns to the figures. The illustrated embodiments of the invention will be best understood by reference to the figures. The following description is intended only by way of example and simply illustrates certain selected exemplary embodiments of the invention as claimed herein.

It should be noted that the flowchart and block diagrams in the figures illustrate the architecture, functionality, and operation of possible implementations of systems, apparatuses, methods and computer program products according to various embodiments of the invention. In this regard, each block in the flowchart or block diagrams may represent a module, segment, or portion of code, which comprises at least one executable instruction for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Specific reference will now be made herebelow to FIGS. 1-3. It should be appreciated that the processes, arrangements and products broadly illustrated therein can be carried out on, or in accordance with, essentially any suitable computer system or set of computer systems, which may, by way of an illustrative and non-restrictive example, include a system or server such as that indicated at 12' in FIG. 5. In accordance with an example embodiment, most if not all of the process steps, components and outputs discussed with respect to FIGS. 1-3 can be performed or utilized by way of a processing unit or units and system memory such as those indicated, respectively, at 16' and 28' in FIG. 5, whether on a server computer, a client computer, a node computer in a distributed network, or any combination thereof.

Figure 1:
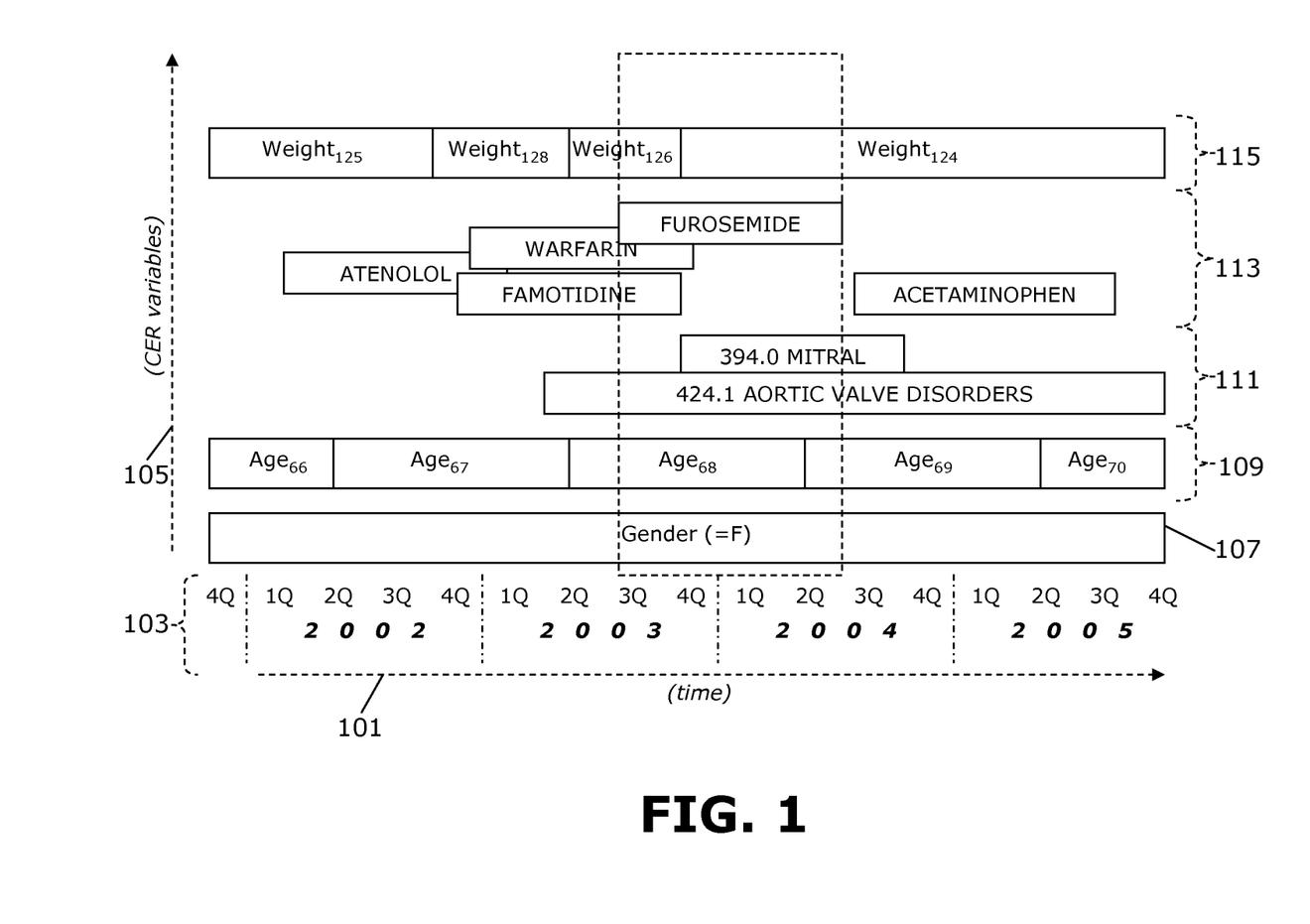
FIG. 1 illustrates a per-patient longitudinal clinical history timeline.
Figure 2:
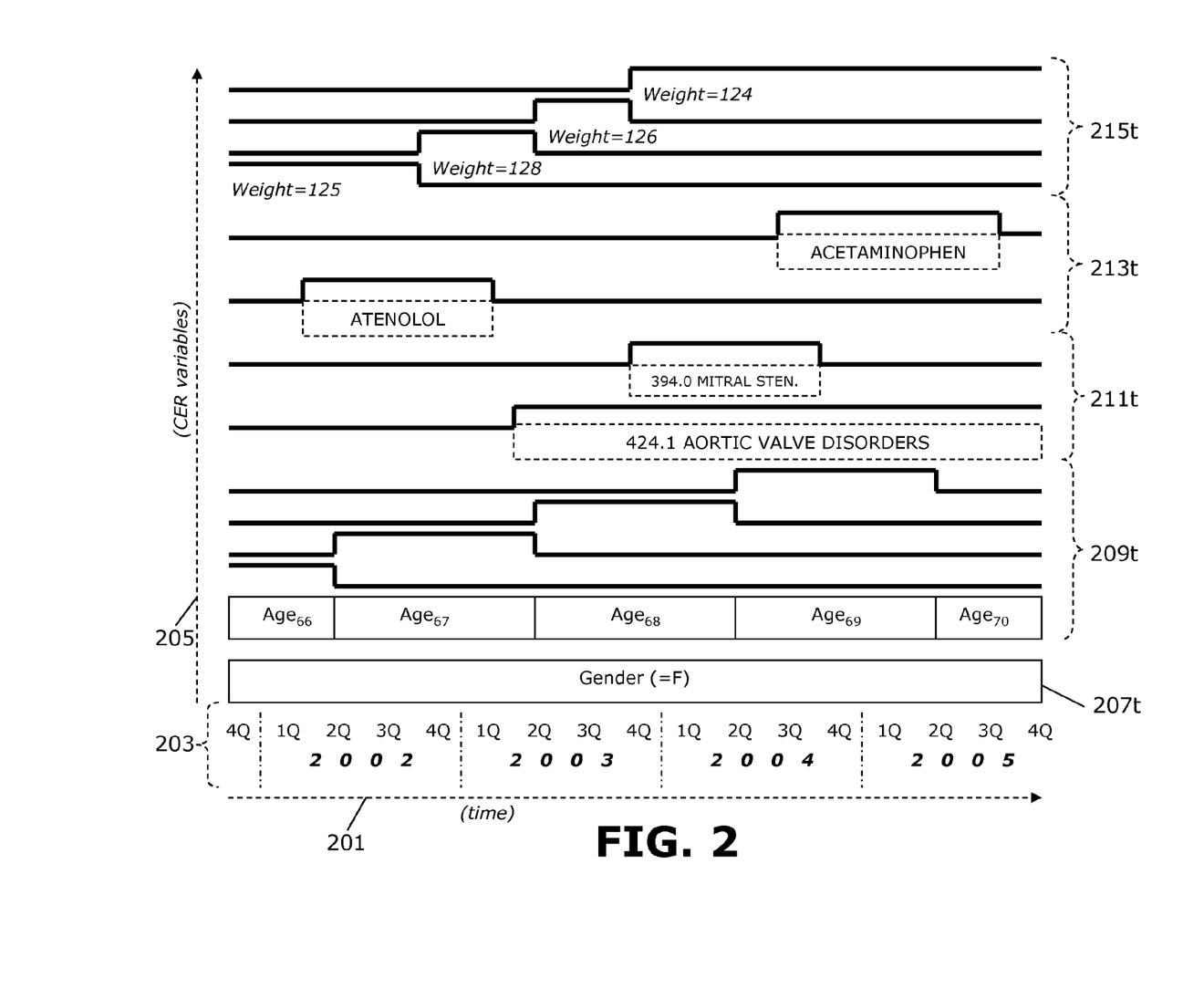
FIG. 2 illustrates a unit time-series model derived from the clinical history timeline of FIG. 1.
Figure 3:
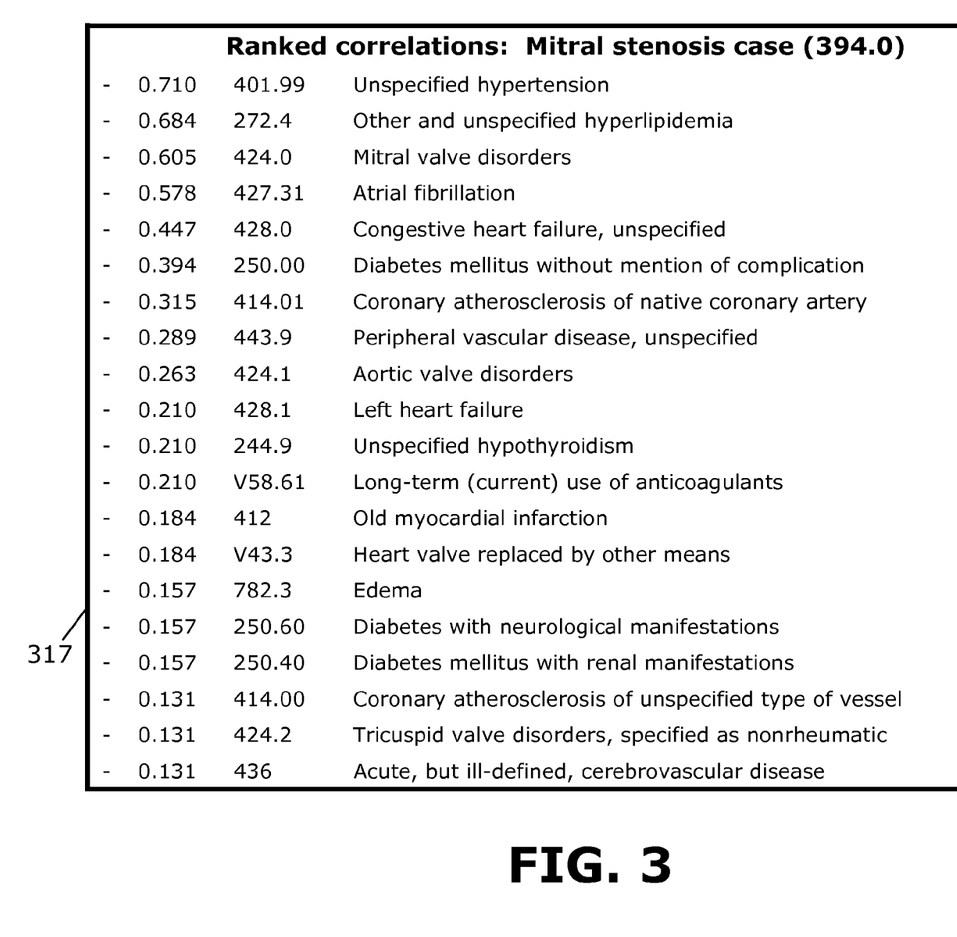
FIG. 3 sets forth ranked disease co-morbidity associations relating to mitral stenosis, by way of a working example.

To facilitate easier reference, in advancing from FIG. 1 to and through FIG. 3, a reference numeral is advanced by a multiple of 100 in indicating a substantially similar or analogous component or element with respect to at least one component or element found in at least one earlier figure among FIGS. 1-3.

Broadly contemplated herein, in accordance with at least one embodiment of the invention, are methods and arrangements for discovering meaningful co-morbidity associations between comparative effectiveness research (CER) variables using time-varying data modeling. The CER variables could be of various types such as symptoms, diseases, medications, other treatments, and outcome. Specifically, there is contemplated herein a longitudinal patient model to address the different types of co-morbidities (causal, co-occurring, etc.). For this, CER variables are represented as a two-dimensional function of variable per patient over time.

To accurately reflect the conditions in a model according to at least one embodiment of the invention, it is assumed that feature extraction modules exist to extract the CER variables from patient data (e.g., which could involve disease label extraction from cardiology reports, by way of an illustrative example). The salient co-morbidities between CER variables are discovered using a search-based ranking framework. For this, there is employed herein a similarity metric per pair of diseases as a functional correlation of the corresponding time series normalized over the patient population. The correlation takes into account both the presence and lack of overlap between the disease time series as well as the time shift needed for causative dependencies. The similarity metric is used to produce a ranked list of correlations per CER variable. Thus a search-based framework is used to discover the association in contrast to traditional data mining methods based on statistical inference.

In accordance with at least one embodiment of the invention, it can be assumed that all relevant clinical features representing comparative effectiveness variables can be extracted from clinical records to populate a longitudinal patient model. Generally, if the original data are in structured form in, e.g., relational databases, then this information can be obtained straightforwardly using JDBC (Java database connectivity) interfaces to databases and making SQL queries. If the data are in unstructured form, then a suitable vocabulary-driven text mining method can be utilized to extract the comparative effectiveness research variables.

As such, in accordance with at least one embodiment of the invention, using the available data from an EMR system, the patient data can be organized on a year-by-year basis in a timeline such as the one shown in FIG. 1. Here, the horizontal axis 101 represents time broken into quarter (three-month) resolution within years (103). The vertical axis 105 shows important CER variables. By way of an illustrative example, such variables can include gender 107, age 109 (here shown as ranging from 66 to 70), diseases 111 (here including aortic valve disorders and mitral stenosis), medications 113 (here including furosemide, acetaminophen, warfarin, famotidine and atenolol) and weight 115 (here shown as ranging from 124 to 128 kilos at different times). Some of these variables are constant (e.g., gender), some are binary (e.g., "yes" or "no"), such as taking or not taking a medication or being diagnosed with a disease, while others are quantized (such as disease severity levels) or continuously changing (such as increasing age).

In accordance with at least one embodiment of the invention, the time period of applicability of CER variable values, with respect to each value involved, can be represented by a unit time series as shown in FIG. 2. Here, the longitudinal clinical history timeline of FIG. 1 has been rendered as a set of unit time series, wherein each time series is "turned on", in binary fashion, for the stated values at the corresponding points in time. Thus, the gender (207*t*) is seen as a constant function, while the time period of applicability of an age (209*t*), a disease label (211*t*), a course of medication (213*t*) and weight (215*t*) is captured by a corresponding unit time series that is turned on during the applicability period.

More formally, in accordance with at least one embodiment of the invention, let the CER variables such as those depicted in FIG. 1 be denoted by $V_1, V_2, \ldots V_M$. Let the set of values taken by a variable $V_1$ be denoted by $v_{i1}, v_{i2}, \ldots v_{ik_i}$. A longitudinal patient model (LPM) is then denoted by a set of unit time series as $$LPM(P) = \qquad (1)$$
$$\{S_P(v_{ik}, t) \mid S_P(v_{ik}, t) > 0 \text{ for some } t, T_{min}(P) \le t \le T_{max}(P)\}$$

where $$S_P(v_{ik}, t) = \begin{cases} 1 & \text{if a value of } v_{ik} \text{ is recorded for CER variable } V_i \text{ for patient } P \text{ at time } t \\ 0 & \text{otherwise} \end{cases}$$

For example, if a diagnosis of 'cardiomyopathy' for the variable 'disease' persisted for a patient between the period ($t_1, t_2$), there will result:

$$S_P(v_{disease, cardiomyopathy}, t) = \begin{cases} 1 & t_1 \le t \le t_2 \\ 0 & \text{otherwise} \end{cases} \qquad (2)$$

In accordance with at least one embodiment of the invention, the disclosure now turns to an algorithm for ranking associations between CER variables. Consider two variables ($V_i, V_j$), and their possible values. ($v_{ik}, v_{jl}$) As an example, a specific disease-drug association could be expressed as ($V_i, V_j$)=(disease, drug) and ($v_{ik}, v_{jl}$)=(mitral stenosis, warfarin). Then, the association between values ($v_{ik}, v_{jl}$) for a patient P over a time span ($T_{min}(P), T_{max}(P)$) is given by the normalized cross-correlation of their associated unit time series as $$R_P(v_{ij}, v_{kl}, \tau) = \frac{\sum_{t=T_{min}(P)}^{T_{max}(P)} S_P(v_{ik}, t) * S_P(V_{jl}, t+\tau)}{\sum_{t=T_{min}(P)}^{T_{max}(P)} S_P(v_{ik}, t) + \sum_{t=T_{min}(P)}^{T_{max}(P)} S_P(v_{jl}, t+\tau)} \qquad (3)$$

Where $0 \le \tau \le \delta$ are the possible time shifts between the two functions. These shifts account for those cases where a drug is taken subsequent to a diagnosis, or a disease is developed following the diagnosis of a disease recorded earlier. This parameter is bounded to disallow far apart associations which could often by due to random chance.

In accordance with at least one embodiment of the invention, the shift with the maximum correlation is then given by $$\bar{R}_P(v_{ik}, v_{jl}) = \max_{\tau}\{R_P(v_{ik}, v_{jl}, \tau)\} \quad (4)$$

Summing these values over all N patients, the result is then:

$$C(v_{ik}, v_{jl}) = \frac{1}{N} * \left(\sum_{P=1}^{N} \bar{R}_P(v_{ik}, v_{jl})\right) \quad (5)$$

By ordering the values of $C(v_{ik}, v_{jl})$, a ranked list of co-associations is obtained. By restricting the value of $\tau$, different types of associations can be modeled. For example, co-occurrences could be handled by making $\tau=0$, positive value of $\tau$ could explore causal relationships, while negative values of $\tau$ could explore clinical history dependencies and prior risk factors.

By way of a working example, in accordance with at least one embodiment of the invention, CER variables in the form of disease-disease associations and disease-drug associations can be considered. Disease labels for patients can be obtained from a variety of sources including billing codes, significant problems, and diagnosis labels derived from cardiac reports, and medications can be obtained directly from a medication history database. Using an enhanced disease label set, and mapping it back to a respective patient's time line, can yield a time unit series as shown in FIG. 2. Starting from each disease label, label, a ranked list of disease co-morbidities is found using the algorithm described hereinabove with respect to equations (3), (4) and (5). As such, FIG. 3 illustrates a table of ranked correlations 317 by way of a possible result of finding disease co-morbidities for the disease label "mitral stenosis" and "hypertension". The values in the first two columns represent correlation score and diagnosis code (in this case, ICD-9 code, i.e., a code as derived from the International Statistical Classification of Diseases and Related Health Problems). Among the matches seen for mitral stenosis are atrial fibrillation, a common known co-occurrence, as well as hyperlipidemia.

To illustrate the power of time-varying interval modeling for disease associations, an algorithm as broadly contemplated herein was compared with a more straightforward approach where only the frequency of co-occurrence is taken into account independent of time. To judge the difference in performance, there was conducted a user study in which 12 cardiac diseases were selected for co-morbidity association finding. Each algorithm generated a top K list (K=10) which was then merged to create a new top K list (after removing redundancies). This "anonymized" merged list was given to three cardiologists for evaluation. For each entry in the ranked list, the cardiologists had to rate an entry as a co-morbidity, a directly-related disease (physiologically), a demographically-correlated disease, or an unrelated disease. The gold standard was based on the pulled ground truth method, i.e., it was derived by combining the first three co-morbidity columns from the three experts. Mean average precision (MAP) was used as the evaluation measure. Precision measures the fraction of relevant co-morbidities found, while the mean average precision emphasizes more relevant matches at higher ranks as given by the formula:

$$AveP = \frac{\sum_{r=1}^{N}(P(r) \times rel(r))}{\text{number of relevant documents}}$$

The co-morbidity associations were examined for 123 disease codes (for which at least 40 patients sample was available). The results of the analysis showed that a method in accordance with at least one embodiment of the invention finds co-morbidities with a higher MAP of 0.16, indicating at least a 32% relative improvement in bringing up more relevant matches.

In accordance with at least one embodiment of the invention, it can be readily understood and appreciated that co-morbidities, as articulated in via comparative effectiveness research variables, can be applied across different modalities. Thus, not only can diseases be compared to diseases, but they can also be compared to medications, laboratory results and other factors.

In accordance with at least one embodiment of the invention, ranked correlations, as discussed hereinabove, can undergo a thresholding step such that correlations above a predetermined quantitative thresholds can be considered "significant". This threshold can be set in essentially any manner deemed suitable.

From the foregoing it can and should be readily appreciated that, in accordance with at least one embodiment of the invention, methods and arrangements such as those broadly discussed and contemplated herein can be employed in determining relevant clinical studies, thus presenting themselves as a noteworthy, viable example of using data mining in developing clinical studies.

Figure 4:
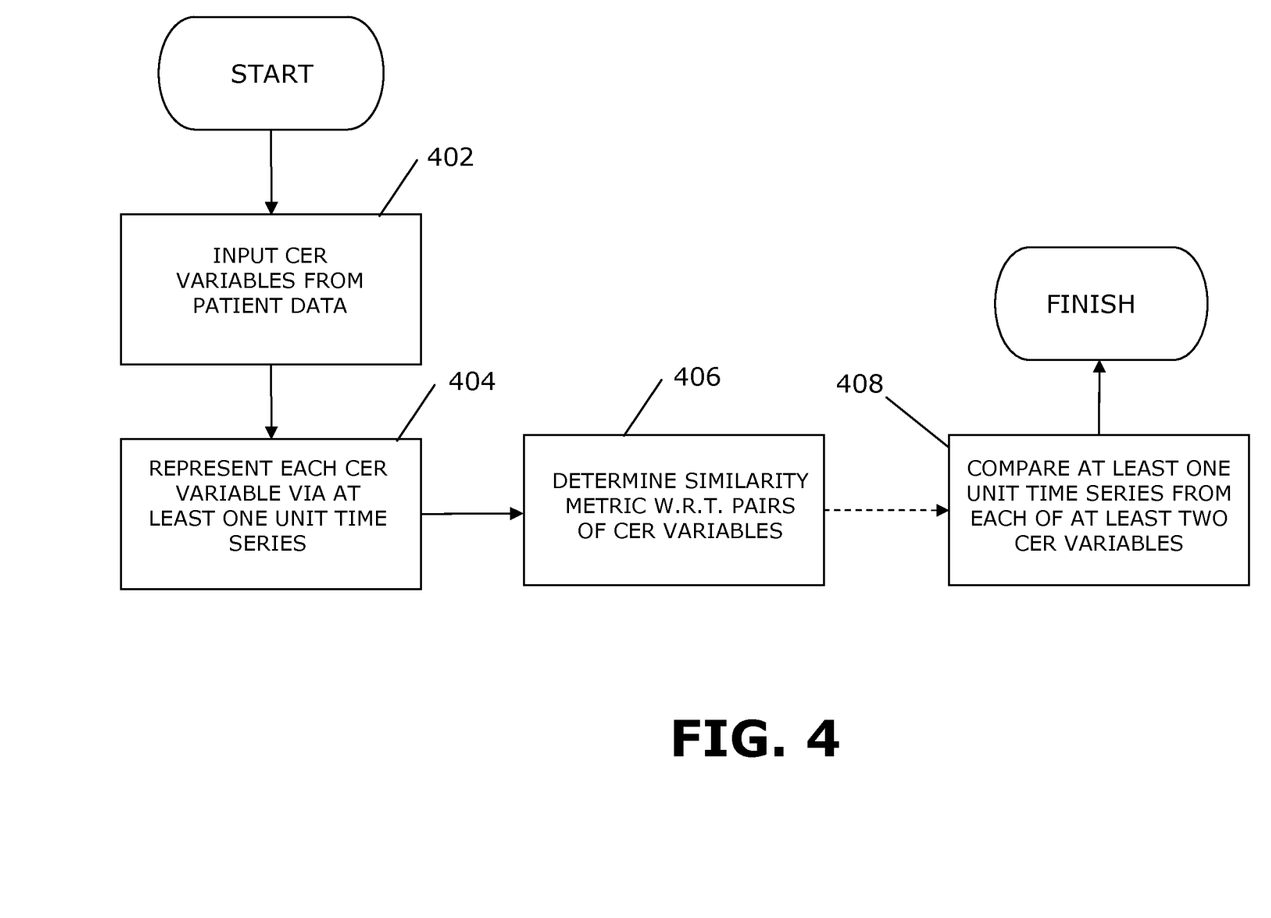
FIG. 4 sets forth a process more generally for ascertaining time-dependent associations.

FIG. 4 sets forth a process more generally for ascertaining time-dependent associations, in accordance with at least one embodiment of the invention. It should be appreciated that a process such as that broadly illustrated in FIG. 4 can be carried out on essentially any suitable computer system or set of computer systems, which may, by way of an illustrative and non-restrictive example, include a system such as that indicated at 12' in FIG. 5. In accordance with an example embodiment, most if not all of the process steps discussed with respect to FIG. 4 can be performed by way a processing unit or units and system memory such as those indicated, respectively, at 16' and 28' in FIG. 5.

As shown in FIG. 4, comparative effectiveness research (CER) variables from patient data are inputted (402). Each CER variable is represented via at least one unit time series (404), and a similarity metric with respect to pairs of CER variables is determined (406). The determining includes comparing at least one unit time series from each of at least two CER variables (408).

Figure 5:
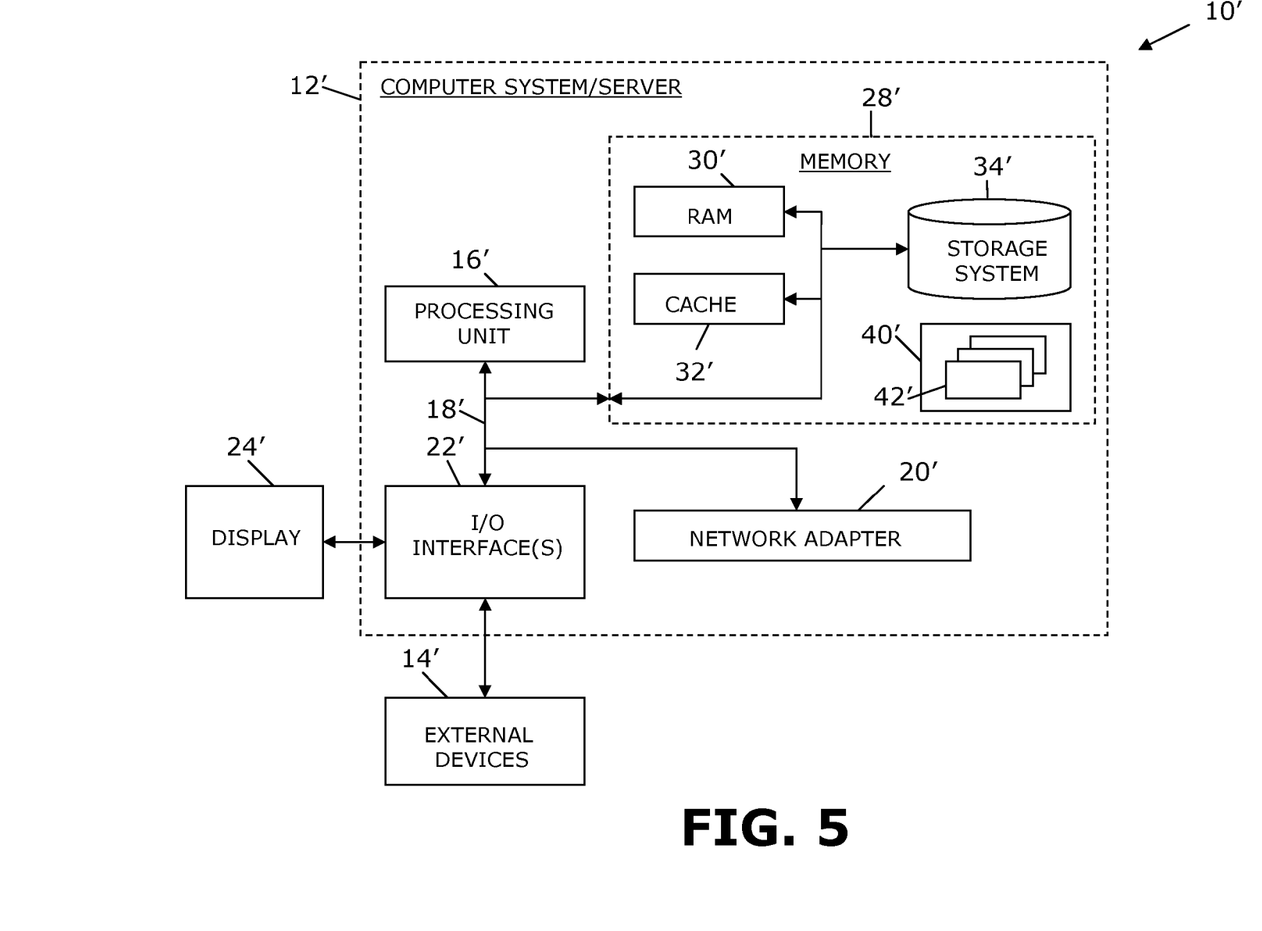
FIG. 5 illustrates a computer system.

Referring now to FIG. 5, a schematic of an example of a cloud computing node is shown. Cloud computing node 10' is only one example of a suitable cloud computing node and is not intended to suggest any limitation as to the scope of use or functionality of embodiments of the invention described herein. Regardless, cloud computing node 10' is capable of being implemented and/or performing any of the functionality set forth hereinabove. In accordance with embodiments of the invention, computing node 10' may not necessarily even be part of a cloud network but instead could be part of another type of distributed or other network, or could represent a stand-alone node. For the purposes of discussion and illustration, however, node 10' is variously referred to herein as a "cloud computing node".

In cloud computing node 10' there is a computer system/server 12', which is operational with numerous other general purpose or special purpose computing system environments or configurations. Examples of well-known computing systems, environments, and/or configurations that may be suitable for use with computer system/server 12' include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12' may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12' may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12' in cloud computing node 10 is shown in the form of a general-purpose computing device. The components of computer system/server 12' may include, but are not limited to, at least one processor or processing unit 16', a system memory 28', and a bus 18' that couples various system components including system memory 28' to processor 16'.

(do we really need to spell these architectures out? The algorithm can be implemented on any SISD, or SIMD machine)

Bus 18' represents at least one of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12' typically includes a variety of computer system readable media. Such media may be any available media that are accessible by computer system/server 12', and includes both volatile and non-volatile media, removable and non-removable media.

System memory 28' can include computer system readable media in the form of volatile memory, such as random access memory (RAM) 30' and/or cache memory 32'. Computer system/server 12' may further include other removable/non-removable, volatile/non-volatile computer system storage media. By way of example only, storage system 34' can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18' by at least one data media interface. As will be further depicted and described below, memory 28' may include at least one program product having a set (e.g., at least one) of program modules that are configured to carry out the functions of embodiments of the invention.

Program/utility 40', having a set (at least one) of program modules 42', may be stored in memory 28' (by way of example, and not limitation), as well as an operating system, at least one application program, other program modules, and program data. Each of the operating systems, at least one application program, other program modules, and program data or some combination thereof, may include an implementation of a networking environment. Program modules 42' generally carry out the functions and/or methodologies of embodiments of the invention as described herein.

Computer system/server 12' may also communicate with at least one external device 14' such as a keyboard, a pointing device, a display 24', etc.; at least one device that enables a user to interact with computer system/server 12'; and/or any devices (e.g., network card, modem, etc.) that enable computer system/server 12' to communicate with at least one other computing device. Such communication can occur via I/O interfaces 22'. Still yet, computer system/server 12' can communicate with at least one network such as a local area network (LAN), a general wide area network (WAN), and/or a public network (e.g., the Internet) via network adapter 20'. As depicted, network adapter 20' communicates with the other components of computer system/server 12' via bus 18'. It should be understood that although not shown, other hardware and/or software components could be used in conjunction with computer system/server 12'. Examples, include, but are not limited to: microcode, device drivers, redundant processing units, external disk drive arrays, RAID systems, tape drives, and data archival storage systems, etc.

It should be noted that aspects of the invention may be embodied as a system, method or computer program product. Accordingly, aspects of the invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the invention may take the form of a computer program product embodied in at least one computer readable medium having computer readable program code embodied thereon.

Any combination of one or more computer readable media may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having at least one wire, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store, a program for use by, or in connection with, an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire line, optical fiber cable, RF, etc., or any suitable combination of the foregoing.

Computer program code for carrying out operations for aspects of the invention may be written in any combination of at least one programming language, including an object oriented programming language such as Java®, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the invention are described herein with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture. Such an article of manufacture can include instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments of the invention have been described herein with reference to the accompanying drawings, it is to be understood that the embodiments of the invention are not limited to those precise embodiments, and that various other changes and modifications may be affected therein by one skilled in the art without departing from the scope or spirit of the disclosure.

What is claimed is:

1. A method comprising:
   inputting comparative effectiveness research variables from patient data;
   representing each comparative effectiveness research variable with at least one unit time series;
   wherein each of the at least one unit time series corresponds to a binary expression of a single value; and
   determining a similarity metric with respect to pairs of comparative effectiveness research variables, said determining comprising comparing at least one unit time series from each of at least two comparative effectiveness research variables.

2. The method according to claim 1, wherein the similarity metric represents a functional correlation of compared unit time series, normalized over a patient population.

3. The method according to claim 2, wherein the functional correlation represents a degree of overlap between compared unit time series.

4. The method according to claim 2, wherein the functional correlation considers at least one time shift representative of a causative dependency.

5. The method according to claim 1, comprising generating a ranked list of correlations per comparative effectiveness research variable.

6. The method according to claim 1, wherein the comparative effectiveness research variables include at least one disease.

7. The method according to claim 6, wherein the comparative effectiveness research variables include at least two diseases.

8. The method according to claim 6, wherein the comparative effectiveness research variables include at least one medication.

9. The method according to claim 6, wherein the comparative effectiveness research variables include at least one member taken from the group consisting of: patient age, patient weight, patient gender.

10. A system comprising:
    at least one processor;
    a storage module; and
    a computer program resident in said system for executing:
    inputting comparative effectiveness research variables from patient data;
    representing each comparative effectiveness research variable via at least one unit time series;
    wherein each of the at least one unit time series corresponds to a binary expression of a single value; and
    determining a similarity metric with respect to pairs of comparative effectiveness research variables; and
    comparing at least one unit time series from each of at least two comparative effectiveness research variables.

11. A computer program product comprising:
    a non-transitory computer readable storage medium having computer readable program code embodied therewith, said computer readable program code being executable by a computer to:
    input comparative effectiveness research variables from patient data;

represent each comparative effectiveness research variable via at least one unit time series;

wherein each of the at least one unit time series corresponds to a binary expression of a single value; and determine a similarity metric with respect to pairs of comparative effectiveness research variables; and compare at least one unit time series from each of at least two comparative effectiveness research variables.

12. The computer program product according to claim 11, wherein the similarity metric represents a functional correlation of compared unit time series, normalized over a patient population.

13. The computer program product according to claim 12, wherein the functional correlation represents a degree of overlap between compared unit time series.

14. The computer program product according to claim 12, wherein the functional correlation considers at least one time shift representative of a causative dependency.

15. The computer program product according to claim 11, wherein said computer readable program code is further executable by the computer to generate a ranked list of correlations per comparative effectiveness research variable.

16. The computer program product according to claim 11, wherein the comparative effectiveness research variables include at least one disease.

17. The computer program product according to claim 16, wherein the comparative effectiveness research variables include at least two diseases.

18. The computer program product according to claim 16, wherein the comparative effectiveness research variables include at least one medication.

19. The computer program product according to claim 16, wherein the comparative effectiveness research variables include at least one member taken from the group consisting of: patient age, patient weight, patient gender.

20. The computer program product according to claim 16, wherein the comparative effectiveness research variables include laboratory results.

* * * * *